(12) United States Patent
Howard

(10) Patent No.: US 6,926,865 B2
(45) Date of Patent: Aug. 9, 2005

(54) METHOD AND APPARATUS FOR DETECTING DNA HYBRIDIZATION

(75) Inventor: John K. Howard, Saratoga, CA (US)

(73) Assignee: Matsushita Electric Industrial Co., Ltd., Osaka (JP)

( * ) Notice: Subject to any disclaimer, the term of this patent is extended or adjusted under 35 U.S.C. 154(b) by 334 days.

(21) Appl. No.: 10/068,853

(22) Filed: Feb. 11, 2002

(65) Prior Publication Data

US 2003/0152929 A1 Aug. 14, 2003

(51) Int. Cl.$^7$ .......................... G01N 15/00; G01N 1/00; C12Q 1/68
(52) U.S. Cl. ........................ 422/68.1; 422/50; 435/6
(58) Field of Search ...................... 422/50, 68.1; 435/6, 435/283.1, 287.1, 287.2

(56) References Cited

U.S. PATENT DOCUMENTS 4,935,207 A * 6/1990 Stanbro et al. ............ 422/68.1
6,627,154 B1 * 9/2003 Goodman et al. ....... 422/82.01

OTHER PUBLICATIONS

Matthews et al., Analytical Biochemistry, vol. 169, pp. 1–25 (1988).*

* cited by examiner

Primary Examiner—Ardin H. Marschel
(74) Attorney, Agent, or Firm—McDermott Will & Emery LLP

(57) ABSTRACT

An apparatus for identifying an unknown DNA sample. The apparatus includes a plurality of detection nodes, each of which is operable for allowing an interaction between a known DNA sample and an unknown DNA sample, and for generating an output signal if hybridization occurs between the known DNA sample and the unknown DNA sample. The apparatus further includes a decoder operative for receiving an input signal indicative of which of the plurality of detection nodes should be selected for processing and for outputting control signals which operate to activate the selected detection node. Further, each of the detection nodes comprises a first floating gate transistor having a conductance value which varies if hybridization occurs between the known DNA sample and the unknown DNA sample contained in the first transistor. This change of conductance value is utilized to generate the output signal which indicates that hybridization has occurred.

20 Claims, 6 Drawing Sheets

METHOD AND APPARATUS FOR DETECTING DNA HYBRIDIZATION

FIELD OF THE INVENTION

This invention relates generally to a system and method of detecting interactions between analyte molecules, and more particularly, to a system and method for determining DNA hybridization.

BACKGROUND OF THE INVENTION

DNA sequencing is becoming a major factor in a number of different emerging scientific fields. For example, DNA sequencing has been utilized in an attempt to diagnosis various diseases. One known method of performing such DNA sequencing/analysis is by matching an array of known DNA sequences (referred to as probes) with an unknown target DNA. More specifically, such a process typically includes placing a number of known DNA sequences on a glass slide. Each of the known DNA sequences are placed at a specific geographic location on the glass slide. A typical glass slide may have the capability of containing 50,000 individual locations, thereby allowing for processing of 50,000 DNA sequences.

Once the known DNA probes are placed in the predetermined locations on the slide, an unknown sample of DNA is placed on the slide. After a set period of time, if the unknown sample of DNA matches any of the known DNA sequences, the unknown DNA sample will hybridize with the known DNA sequence at the given location of the known DNA sequence. Assuming there is a match, the unknown sample DNA is identified as the DNA sequence with which the hybridization occurred.

In accordance with the foregoing technique, it is necessary to determine whether hybridization has occurred as well as the specific location of the hybridization so as to allow for a correlation between the location of the hybridization and the corresponding known DNA sequence. One common method of performing this determination is by an optical detection technique. In accordance with this technique, first, after allowing sufficient time for hybridization between the known DNA sequences and the unknown sample DNA, the slide is treated such that all un-hybridized DNA are removed from the slide. Next, an optical detection technique is utilized to determine the presence of a fluorescent molecule, which is attached to each known DNA sequence prior to the hybridization process. Specifically, if hybridization has occurred, the fluorescent molecule (i.e., die) attached to the known DNA sequence will be present even after the known DNA sequence has hybridized with the unknown DNA sample (if there was no match, all the known DNA sequences along with the fluorescent molecule would be removed from the slide during the aforementioned treatment process). Accordingly, by utilizing, for example, a laser and a photo detector, it is possible to determine the presence and location of the fluorescent molecule, which identifies the sample DNA by correlating the position of the fluorescent molecule with the location of the known DNA sequences. Typically, the instrument utilized to determine the presence of the fluorescent molecule is a desktop micro-array scanner.

Specific examples of such known optical detection systems and methods are set forth in U.S. Pat. No. 5,578,832, "Method And Apparatus For Imaging A Sample On A Device" issued to Trulson et al., and U.S. Pat. No. 5,631,734, "Method And Apparatus For Detection Of Fluorescently Labeled Materials", issued to Stem et al. Both of the foregoing patents are hereby incorporated by reference. Utilizing a method similar to that described above both of the foregoing patents employ the use of a fluorescent molecule, such as fluorophore and biotin, which is attached to the known DNA sequence. An optical system is then utilized to determine whether hybridization has occurred by measuring fluorescence activated between the sample DNA and the known DNA.

Another known technique for identifying unknown DNA sequences is disclosed in U.S. Pat. No. 6,203,983, which is also hereby incorporated by reference. As disclosed therein, a method is presented which allows for the detection of a chemical interaction (e.g., DNA hybridization) without having to modify (i.e., label) the known DNA sequence. Specifically, the method entails formation of a mechanical cantilever mechanism capable of physical movement in the upward and downward direction. The cantilever mechanism is arranged in conjunction with the sample DNA and known DNA such that hybridization of the DNA will result in the physical deflection of the cantilever, which can be detected, thereby allowing for identification of the sample DNA.

Notwithstanding the foregoing chemical interaction detection systems utilized to identify unknown DNA samples, problems remain. For example, the systems utilizing optical detection means to detect fluorescent markers can be expensive. Moreover, the time requirements for operating the system can be exceedingly long as a typical array to be analyzed may contain on the order of 50,000 DNA samples, which need to be scanned on a one-by-one basis during processing. Systems utilizing micromechanical devices, such as the cantilever mechanism disclosed in the '983 patent, require elaborate semiconductor processing techniques during the formation thereof, which increase the costs associated with the resulting test arrays. Moreover, such devices are exceedingly subject to failure due to mechanical nature of the operation of the array, thereby reducing the overall reliability of the resulting array.

Accordingly, there remains a need for providing a detection system capable of identifying unknown DNA samples that eliminates the need for the optical scanner so as to allow for a reduction in both the time and cost associated with performing the analysis. In addition, it is desirable that the detection system eliminate the need for micromechanical devices so as to improve the overall reliability of the system.

It is the object of the present invention to correct the foregoing deficiencies in the prior art.

SUMMARY OF THE INVENTION

In general, the present invention relates to a DNA detection system that provides for identification of the unknown DNA in an electronic manner. The DNA detection system of the present invention eliminates the need for utilizing an optical scanner during the detection process, and the elimination of micromechanical devices from the detection system.

In a first exemplary embodiment, the present invention relates to an apparatus for identifying an unknown DNA sample. The apparatus comprises a plurality of detection nodes, each of which is operable for allowing an interaction between a known DNA sample and an unknown DNA sample, and for generating an output signal if hybridization occurs between the known DNA sample and the unknown DNA sample. The apparatus further comprises a decoder operative for receiving an input signal indicative of which of the plurality of detection nodes should be selected for processing and for outputting control signals which operate to activate the selected detection node. Further, each of the detection nodes comprises a first floating gate transistor having a conductance value which varies if hybridization occurs between the known DNA sample and the unknown DNA sample contained in a floating gate terminal of the first floating gate transistor. This change of conductance is utilized to generate the output signal which indicates that hybridization has occurred.

The present invention also relates to a method of identifying an unknown DNA sample. The method comprises the steps of generating a first reference voltage signal; generating a second reference voltage signal utilizing a first floating gate transistor having a known DNA sample disposed on a floating gate terminal thereof and which is capable of receiving the unknown DNA sample, where the first floating gate transistor has a conductance value that varies if hybridization occurs between the known DNA sample and the unknown DNA sample when the unknown DNA sample is delivered to the floating gate terminal of the first floating gate transistor. The method further includes generating an output signal representing a difference between the first reference voltage signal and the second reference voltage signal, which is utilized to determine if hybridization has occurred.

As described in further detail below, the present invention provides significant advantages over the prior art. Most importantly, the method and system of detecting/identifying unknown DNA of the present invention allows for the elimination of the need for utilizing an optical scanner during the detection process, and allows for real-time detection, of unknown DNA. As such, the present invention allows for a reduction in the overall cost and time associated with performing the detection analysis.

Another advantage of the present invention is that it eliminates the need for utilizing micromechanical devices in the detection system, thereby increasing the overall reliability of the detection system.

Additional advantages of the present invention will become apparent to those skilled in the art from the following detailed description of exemplary embodiments of the present invention.

The invention itself, together with further objects and advantages, can be better understood by reference to the following detailed description and the accompanying drawings.

DETAILED DESCRIPTION OF THE DRAWINGS

The following detailed description relates to a novel DNA detection system that allows for electronic detection/identification of unknown DNA The description of the exemplary embodiment of the system sets forth numerous specific details regarding the configuration of the system. It will be obvious, however, to one skilled in the art that these specific details need not be employed to practice the present invention. Clearly, other configurations and implementations of the DNA detection system are possible.

Figure 1:
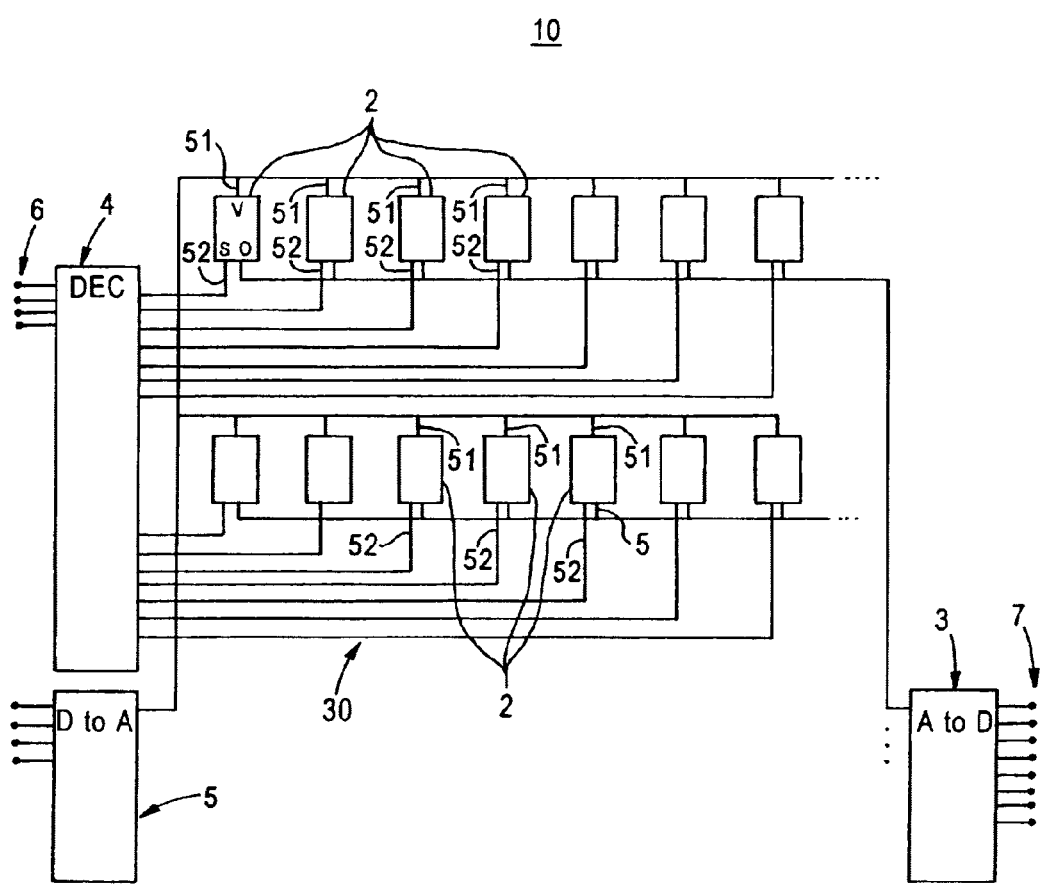
FIG. 1 is a block diagram of an exemplary embodiment of the DNA detection system in accordance with the present invention.

FIG. 1 illustrates a block diagram of an exemplary embodiment of the DNA detection system 10 in accordance with the present invention. Referring to FIG. 1, the system 10 comprises a plurality of addressable detection nodes 2, a node selection decoder 4, a D/A converter 5 and an A/D converter 3. As explained in further detail below, each of the plurality of detection nodes 2 has an identical structure and is capable of comparing a known DNA sample with an unknown DNA and outputting an electronic signal if the given DNA sample and unknown DNA hybridize (i.e., match). Each addressable detection node 2 comprises three signal lines coupled thereto. The first is a variable input voltage signal line 51 for receiving a voltage signal output by D/A converter 5. A variable voltage source (not shown) is coupled to the input of the D/A converter 5 and is utilized to vary the input voltage applied to each addressable detection node 2. The level of the voltage input into the addressable detection nodes 2 is determined by empirical methods and varies depending on the particular DNA assay being analyzed.

Figure 2:
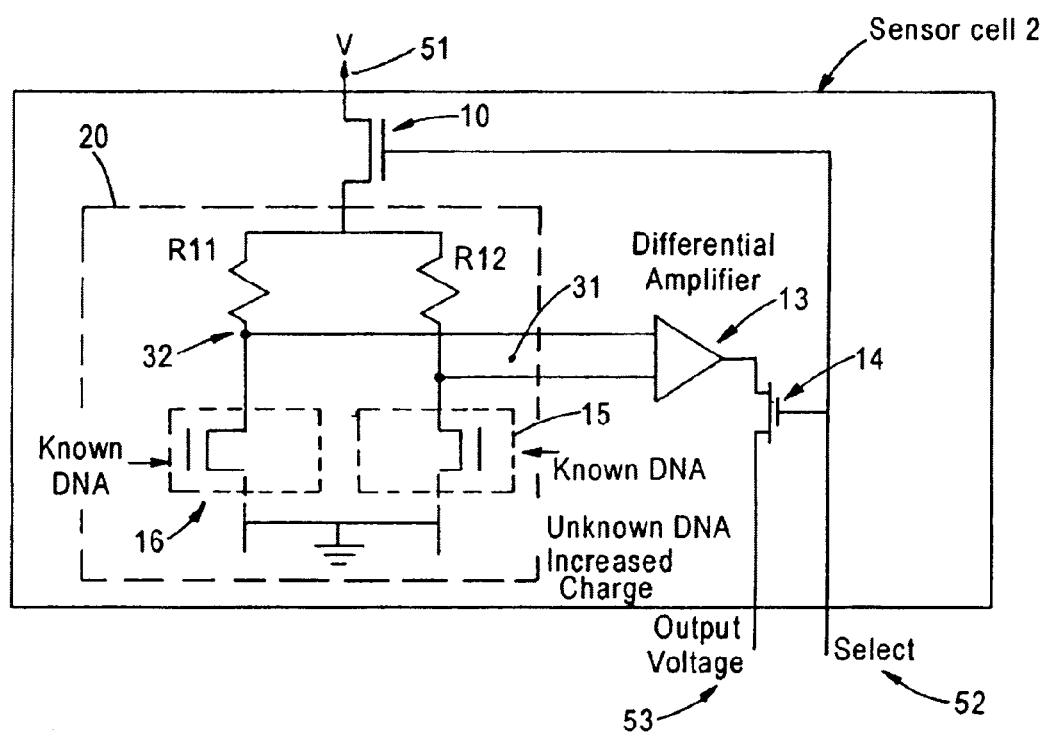
FIG. 2 is an exemplary schematic diagram illustrating one embodiment of a detection node utilized on the DNA detection system illustrated in FIG. 1.

The second signal line is the select line 52, which as explained in conjunction with FIG. 2 is utilized to select a given addressable detection node 2 for analysis. As shown, each select line 52 is also coupled to the output of the node selection decoder 4. In the preferred embodiment, node selection decoder 4 functions to activate a single select line 52 at a time so as to allow for analysis of the corresponding detection node 2. The detection node 2 to be selected is determined by the digital control signal 6 coupled to the input of the node selection decoder 4. The digital control signal 6 is generated by a computer/controller (not shown). As stated, the node selection decoder 4 is utilized to select any one of the detection nodes 2 by inputting a signal corresponding to the address of the desired detection node 2 into the node selection decoder 4. During operation, for example, the selection node decoder 4 may be controlled so as to sequentially activate each detection node 2 so as to allow for determination of whether or not the known DNA and the unknown DNA in the given detection node 2 hybridized.

The third signal line 53 is an output line which functions to couple the output signal generated by the given detection node 2 to the A/D converter 3. As explained in further detail below, the output signal of a given detection node 2 exhibits a first voltage level if the known DNA and the unknown DNA in the given detection node 2 hybridize, and exhibits a second voltage level if the known DNA and the unknown DNA do not hybridize. The output line 53 of a given detection node 2 is activated upon selection of the given detection node 2 by the selection node decoder 4. Accordingly, in the preferred embodiment, only one output signal line 53 is active at a time. The output of the A/D converter 3 is coupled to a computer/controller (not shown) for analysis and recordation of the data. For example, assuming the voltage level of the output signal of detection node "X" indicates hybridization has occurred, as the identification of the known DNA deposited in detection node "X" is recorded and stored in memory, upon receiving the signal indicating hybridization has occurred, the computer/controller retrieves the data associated with detection node "X", which identifies the known DNA contained in detection node "X", and labels the unknown DNA placed in detection node 2 equal to the known DNA.

FIG. 2 is an exemplary schematic diagram illustrating one embodiment of a detection node 2, which is also referred to as a biosensor cell. Referring to FIG. 2, each biosensor cell 2 includes a voltage divider circuit 20 comprising resistors R11 and R12, floating gate transistors 15 and 16, a differential amplifier 13 and transistors 10 and 14 which function to activate the given biosensor cell 2 and to couple the output of the biosensor cell 2 to the A/D converter 3. The operation of the biosensor cell 2 is as follows.

First, in order to select/activate a given biosensor cell 2, the corresponding selection line 52 must be made active by the selection node decoder 4. Activation of the selection line 52 functions to turn on transistors 10 and 14. As a result, the voltage signal "V" on the first signal line 51 is coupled to the voltage divider circuit 20 and the output of the differential amplifier 13 is coupled to the output signal line 53. The voltage divider circuit 20 essentially comprises two voltage divider circuits. The first divider circuit is formed by resistor R11 and floating gate transistor 16, and the second divider circuit is formed by resistor R12 and floating gate transistor 15. The first divider circuit generates a first reference voltage at node 32, which is coupled to one input of the differential amplifier 13, and the second divider circuit generates a second reference voltage at node 31, which is coupled to a second input of the differential amplifier 13.

Resistors R11 and R12 are fixed resistors of equal value and are fabricated utilizing standard semiconductor processing techniques. As explained below in further detail, floating gate transistors 15 and 16 are both formed such that known DNA is placed on the floating gate thereof. In addition, floating gate transistor 15 is fabricated so as to allow for receipt of unknown DNA on the floating gate. Floating gate transistor 16 is formed such that it cannot receive unknown DNA. It is noted that the design of floating gate transistors is well known, such as, for example, that disclosed in U.S. Pat. No. 6,284,637, which is hereby incorporated by reference. Exemplary structures of floating gate transistors 15 and 16 are described in detail further below. However, it is noted that the exposure and/or non-exposure to the known DNA and the unknown DNA can be accomplished utilizing various capillary designs for transporting such material as is well known by those of skill in the art. Indeed, as the preferred embodiment of the present invention entails forming the detection system on a single semiconductor chip, in one embodiment, after formation of the transistors and the other circuitry noted above, an additional layer is formed on the semiconductor structure which includes the necessary capillary design so as to allow unknown DNA to be delivered to the floating gate of transistor 15. The known DNA would be placed on the floating gates of transistors 15 and 16 of each biosensor cell 2 during the fabrication process prior to placement of the additional layer on the semiconductor structure.

For example, during the formation of transistors 15 and 16, a robotic spotter utilizing a normal pen or ink jet technology can be utilized to apply known DNA to the floating gate of each transistor 15 and 16 of each biosensor cell 2. It is noted that while it is possible to apply the known DNA to the floating gates of transistors 15 and 16 during the fabrication process, it is also possible to form the transistors such that the known DNA can be applied subsequent to the formation of the transistors. In such an embodiment, the aforementioned additional layer formed on the semiconductor structure would include additional capillary design structure so as to also allow known DNA to be delivered to the floating gate of each transistor.

Figure 3:
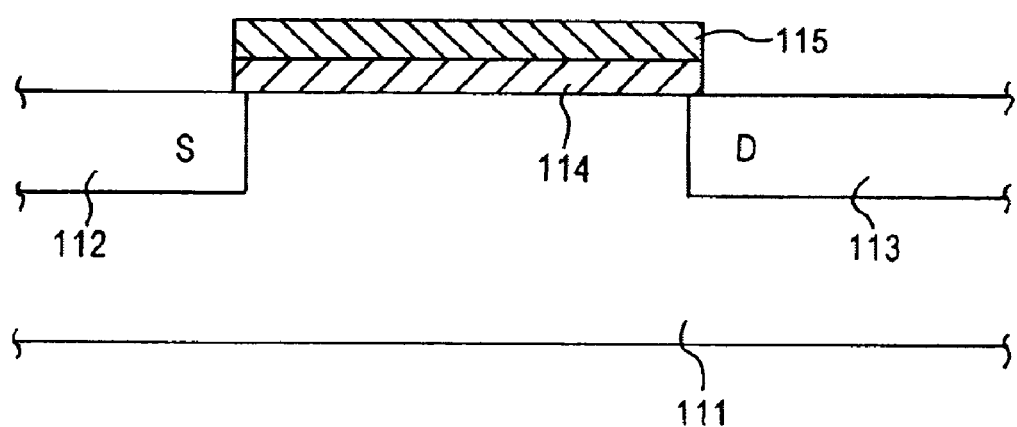
FIG. 3 illustrates an exemplary embodiment of a floating gate transistor utilized in the detection node illustrated in FIG. 2.

FIG. 3 illustrates an exemplary embodiment of a floating gate transistor utilized in accordance with the present invention. Referring to FIG. 3, the exemplary floating gate transistor comprises a substrate 111, and a source region 112 and drain region 113. In addition, the transistor comprises a first isolation layer 114 formed over the substrate 111, and a polysilicon floating gate 115 (also referred to as the floating gate terminal) formed over the isolation layer 114. When known DNA is supplied to the floating gate of each transistor, as DNA is highly negatively charged, a negative charge is placed on the floating gate 115. This negative charge results in current flow in the given transistor (15 and 16). In accordance with the present invention, a sufficient amount of the known DNA should be placed on the floating gate such that current flow is induced and detectable. Moreover, the same amount of known DNA is placed on the floating gate of transistors 15 and 16 of each biosensor cell such that the resulting current flowing through transistors 15 and 16 is equal.

In operation, once the known DNA is placed on the floating gate of each transistor 15 and 16 of each biosensor cell 2, a current of equal value flows in each of the voltage divider circuits contained in voltage divider 20. Specifically, referring to FIG. 2, both the voltage divider circuit comprising resistor R11 and transistor 16 and the voltage divider circuit comprising resistor R12 and transistor 16 have currents of equal value flowing therethough. As a result, the voltage levels at node 32 and node 31 of the voltage divider circuits are equal. Thus, the output of the differential amplifier 13 is zero.

Continuing, when unknown DNA is supplied to the floating gate of transistor 15, if the unknown DNA matches the known DNA sample already contained in the floating gate of transistor 15, the known DNA sample hybridizes to the unknown DNA which effectively increases the negative charge applied to the floating gate of transistor 15, which results in an increase in current flowing through transistor 15, and the second voltage divider formed by transistor 15 and resistor R12. It is noted that it is preferable that a sufficient quantity of unknown DNA be deposited such that in the event of hybridization the resulting increase in negative charge on the floating gate results in a measurable change in the current flow through the transistor 15. For example, in one embodiment, the amount of unknown DNA utilized is sufficient to at least effectively double the charge on the given floating gate terminal. It is noted that the unknown DNA that does not hybridize is washed away utilizing known techniques so as to remove the un-hybridized DNA.

As a result, when an unknown DNA and a known DNA match (i.e., hybridize) in a given biosensor cell 2, the current flowing through the transistor 15 increases, thereby resulting in a change in voltage at node 31. Specifically, as the current increases in transistor 15, the voltage at node 31 decreases in accordance with Ohm's law as the voltage drop across resistor R12 increases. This change in voltage at node 31 generates a difference between the voltage at node 31 and the voltage at node 32. This difference in voltage is amplified by differential amplifier 13 and output to the A/D converter 3, and coupled to a data analyzer/computer (not shown) for processing. In particular, when the difference voltage exceeds some predetermined threshold value, the unknown DNA input into transistor 15 is deemed to be the same as the known DNA contained in transistor 16 of the same biosensor cell 2.

As noted above, in the preferred embodiment, transistors 16 and transistor 15 have the same amount of the unknown DNA material deposited on the respective floating gate terminals. As such, in the event there is no match between the unknown DNA and the known DNA subsequently placed on the floating gate of transistor 15 the voltage values at nodes 31 and 32 will be substantially equal, thereby generating a substantially zero voltage difference at the inputs to the differential amplifier 13. However, it is noted that it is also possible to design a detection system such that the different values of the voltage levels at nodes 31 and 32 occur even when there is no hybridization. In such an embodiment, the data analyzer would be pre-programmed with the non-zero difference value (i.e., other than zero) input into the differential amplifier in the event no matched occurs. The data analyzer would then treat this non-zero difference value as the normal state (i.e., no match) and determine the occurrence of hybridization by judging the change in voltage relative to the non-zero difference value. It is further noted that the amount of DNA to be deposited on the floating gate of each transistor of the biosensor cells necessary to establish measurable current values can be determined by empirical methods and will likely vary depending on the given DNA assay under consideration.

Figure 4:
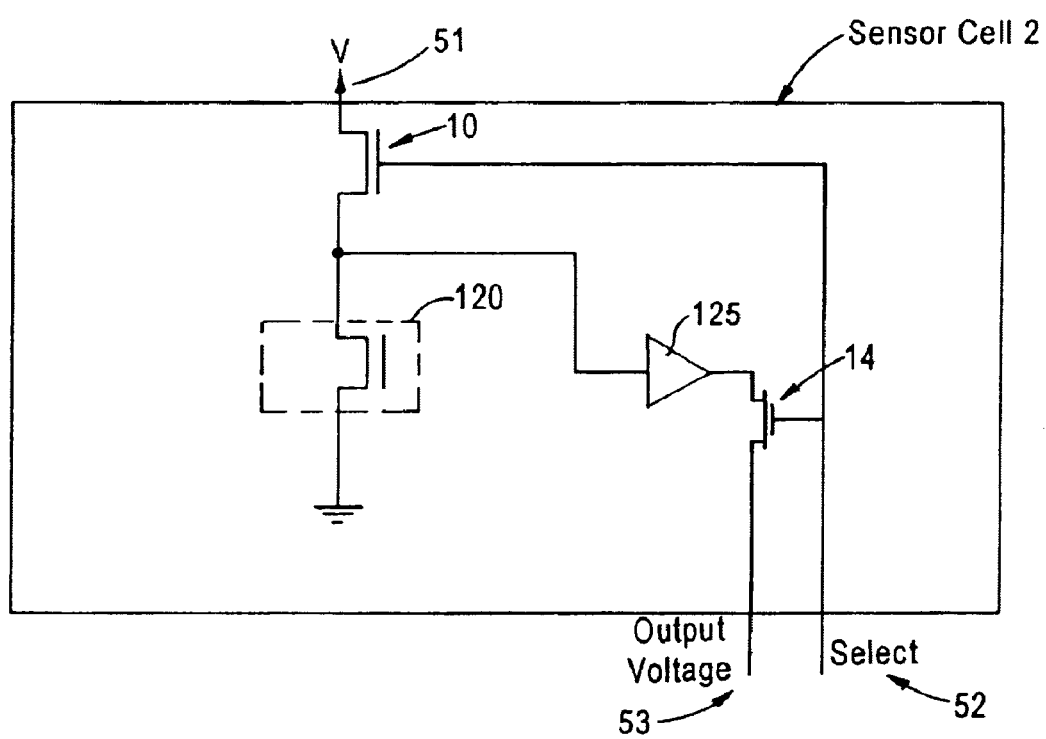
FIG. 4 is an exemplary schematic diagram illustrating a second embodiment of a DNA detection system in accordance with the present invention.

FIG. 4 illustrates an exemplary schematic diagram of a second embodiment of a DNA detection system in accordance with the present invention. Referring to FIG. 4, in the second embodiment the biosensor cell 200 is modified such that the voltage divider circuit 20 and the differential amplifier 13 are eliminated from the design and replaced with transistor 120 and a sense amplifier 125. The remaining components contained in the biosensor cell 200 are the same as those disclosed above in FIG. 2 and they perform in the same manner as detailed above. Furthermore, the composition and operation of transistor 120 of the second embodiment is the same as that of transistor 15 of the first embodiment discussed above.

In accordance with the operation of the second embodiment, upon placement of the known DNA on the floating gate of transistor 120, the current/conductance of transistor 120 is measured by sense amplifier 125 so as to establish a known current/conductance value. Thereafter, the unknown DNA is deposited on the floating gate of transistor 120 in the same manner as detailed above. After depositing the unknown DNA, the current/conduction of transistor 120 is measured again. In the event hybridization has occurred, there will be a significant increase (e.g., at least double) in the negative charge applied to the floating gate of transistor 120, which as described above, results in a significant increase in the current/conductance of transistor 120. Assuming the current/conductance value is above a predefined value, which is determined utilizing the current/conductance value of the transistor 120 prior to depositing the unknown DNA, the unknown DNA supplied to transistor 120 is deemed to match with the known DNA contained in the transistor 120. It is noted that the second embodiment of the present invention is essentially monitoring the current value of transistor 120 to determine if a change in current value occurs upon depositing the unknown DNA. A change in the current value indicates that hybridization has occurred, and that the unknown DNA matches the DNA contained in the given biosensor cell 2. The second embodiment of the present invention advantageously allows for the elimination of transistor 16 and, more importantly, the need to deposit known DNA samples in each transistor 16 contained in each biosensor cell 2.

It is noted that in accordance with both the first and second embodiments of the present invention, the surface of the floating gate of transistors 15 and 16 is coated with a hydrophilic material so as to allow the binding of immobilization chemistry (i.e the binding of the DNA material to the floating gate).

Figure 5:
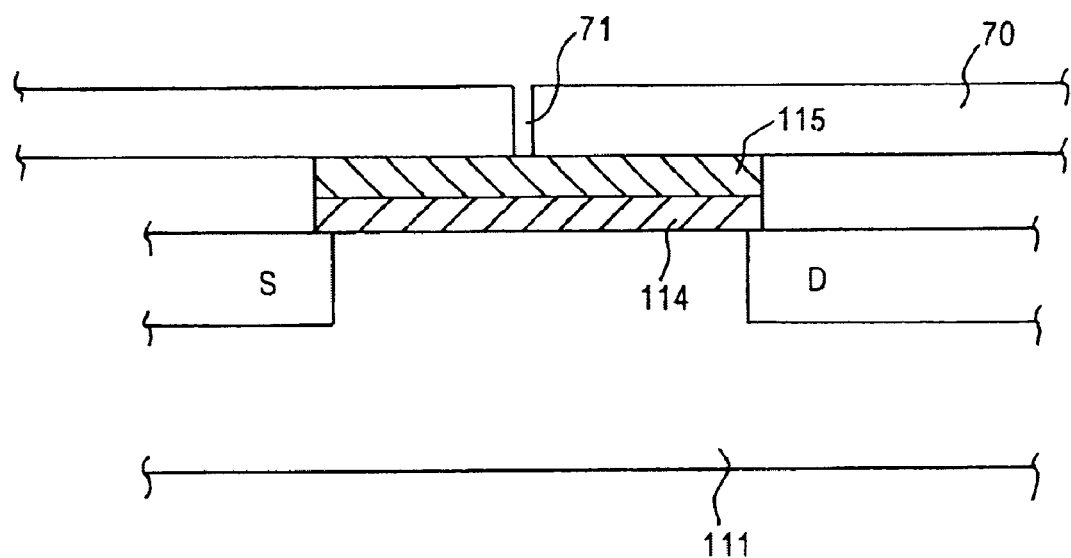
FIG. 5 illustrates an example of a micro-machined manifold layer comprising a plurality of capillaries for delivery of DNA samples to the floating gate of transistors contained in the biosensor cell.

Once the known DNA is deposited on the floating gates of transistors 15 and 16, a micro-machined manifold layer 70 is bonded to the upper surface of the semiconductor chip. Referring to FIG. 5, the micro-machined manifold layer 70 comprises a plurality of capillaries 71 (i.e., passageways), which allow for subsequent delivery of the unknown DNA sample to the floating gate of each transistor 15 of each biosensor cell 2 in the array. The design of capillary networks capable of performing this function are known in the art. It is noted that in the foregoing embodiments the capillaries do not provide access to the floating gate of transistor 16 of any biosensor cell 2. However, as a variation to the foregoing, as noted above, it is possible to design the capillary network so as to allow for the deposition of known DNA to the floating gates of transistors 15 and 16 of each biosensor cell 2 and the subsequent deposition of the unknown DNA to the floating gate of transistor 15 of each biosensor cell.

Accordingly, in operation, the unknown DNA is supplied to the floating gate of each transistor 15 of each biosensor cell 2 via the capillary network. Once the unknown DNA is applied, the processing and operation of the apparatus is as set forth above.

Figure 6:
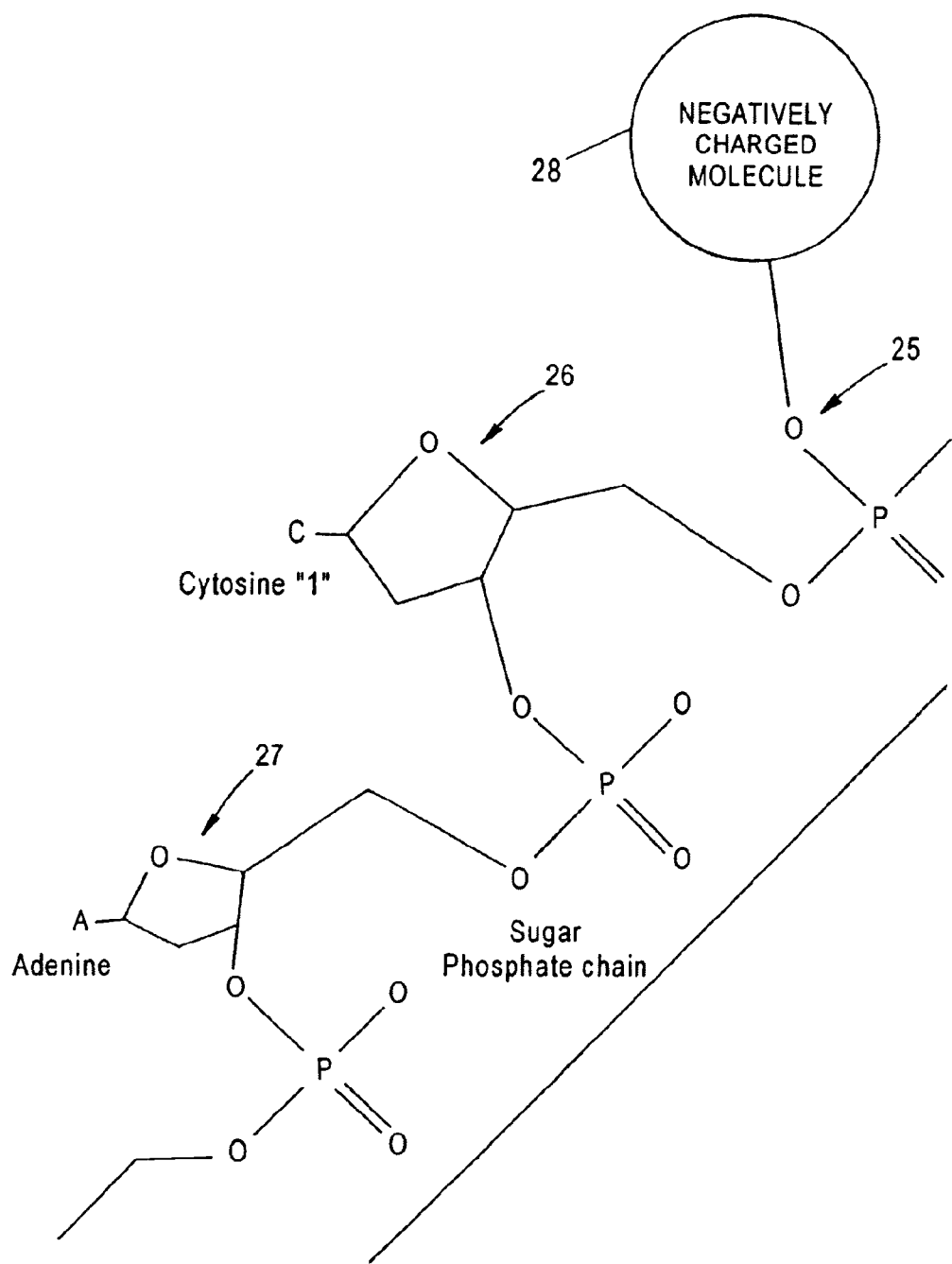
FIG. 6 is an exemplary molecular diagram illustrating the attachment of a highly negative charged molecule to a target DNA molecule.

FIG. 6 is an exemplary molecular diagram illustrating the attachment of a highly negative charged molecule to a known DNA molecule, which is utilized in an alternative embodiment of the present invention. More specifically, in the event that the change in the negative charge on the floating gate of the transistor 15 resulting from the hybridization of the known DNA and unknown DNA is insufficient to produce a detectable change in current (which may occur as the result of the given DNA sample being analyzed), it is possible to tag the known DNA sample deposited in transistor 15 with a highly negative charged molecule prior to depositing the known DNA sample on the floating gate of transistor 15. In the event of hybridization, the highly negative charged molecule remains on the floating gate terminal, thereby further increasing the negative charge applied thereto. FIG. 6 illustrates the attachment of a molecule of barium strantum titanate to the known DNA molecule. Of course, any other highly negative charged molecule can be utilized. It is noted that the DNA sample illustrated in FIG. 6 is a sugar phosphate chain.

As described above, the present invention provides significant advantages over the prior art. Most importantly, the method and system of detecting/identifying unknown DNA of the present invention allows for the elimination of the need for utilizing of an optical scanner during the detection process, and allows for real-time detection of unknown DNA. As such, the present invention allows for reduction in the overall cost and time associated with performing the detection analysis.

Another advantage of the present invention is that it eliminates the need for utilizing micromechanical devices in the detection system, thereby increasing the overall reliability of the detection system.

Yet another advantage is that the system of the present invention can be implemented in a single semiconductor integrated circuit chip, and the number of biosensor cells contained on the chip can vary from chip to chip depending on the intended application. Accordingly, a medical technician can simply supply the unknown DNA to the system chip and the system chip can determine if the unknown DNA matches any of the known DNA in the system chip without any further analysis or measurements being performed by the technician.

Numerous variations of the foregoing embodiments of the present invention are also possible. For example a comparator can be included in each biosensor cell, which functions to generate an output signal only if the output of the differential amplifier is a above some predetermined level. In such an embodiment, the comparator functions to output a signal (e.g., logical "1") only if hybridization occurs between the known DNA sample and the unknown DNA.

It is further noted that while the detection system of the present invention has been described with regard to identifying unknown DNA samples, it can also be utilized in conjunction with the identification of other chemical assays.

Although certain specific embodiments of the present invention have been disclosed, it is noted that the present invention may be embodied in other forms without departing from the spirit or essential characteristics thereof. The present embodiments are therefore to be considered in all respects as illustrative and not restrictive, the scope of the invention being indicated by the appended claims, and all changes that come within the meaning and range of equivalency of the claims are therefore intended to be embraced therein.

What is claimed is:

1. An apparatus for identifying an unknown DNA sample, said apparatus comprising:
   a plurality of detection nodes, each of said detection nodes operable for allowing an interaction between a known DNA sample and an unknown DNA sample, and for generating an output signal if hybridization occurs between said known DNA sample and said unknown DNA sample; and
   a decoder operative for receiving an input signal indicative of which of said plurality of detection nodes should be selected for processing, and for outputting control signals which operate to activate said selected detection node;
   wherein each of said detection nodes includes a first floating gate transistor comprising a floating gate terminal having said known DNA sample and said unknown DNA sample disposed thereon, said first floating gate transistor having a conductance value which varies if hybridization occurs between said known DNA sample and said unknown DNA sample contained in said detection node, said change in said conductance value is operative for generating said output signal, and
   wherein in said known DNA sample has a highly negative charged molecule attached thereto.

2. The apparatus of claim 1, wherein said output signal has an amplitude which varies in accordance with variations of said conductance value of said first floating gate transistor.

3. The apparatus of claim 1, wherein each detection node further comprises:
   a first voltage divider circuit capable of generating a first reference voltage signal;
   a second voltage divider circuit capable of generating a second reference voltage signal; and
   a differential amplifier for receiving said first reference voltage signal and said second reference voltage signal as input signals, and for generating said output signal, said output signal representing a difference between said first reference voltage signal and said second reference voltage signal;
   wherein said second voltage divider circuit includes said first floating gate transistor, and a variation in said conductance value of said first floating gate transistor causes a corresponding variation in said second reference voltage signal.

4. The apparatus of claim 3, wherein said detection node further comprises:
   a first pass transistor operative for coupling a voltage supply to said first voltage divider and said second voltage divider; and
   a second pass transistor operative for coupling an output of said differential amplifier to an output port of said detection node;
   said first pass transistor and said second pass transistor being activated by said control signals output by said decoder.

5. The apparatus of claim 1, wherein hybridization of said known DNA sample and said unknown DNA sample causes an increase in a charge on said floating gate terminal of said first floating gate transistor, said increase in said charge on said floating gate terminal generating an increase in said conductance value of said first floating gate transistor.

6. The apparatus of claim 3, wherein said first voltage divider circuit includes a second floating gate transistor having said known DNA sample disposed on a floating gate terminal of said second floating gate transistor, said second floating gate transistor comprising the same amount of the known DNA sample as said first floating gate transistor such that said first reference voltage signal and said second reference voltage signal are equal if said known DNA sample and said unknown DNA sample do not hybridize in said first floating gate transistor.

7. A biosensor cell for identifying an unknown DNA sample, said cell comprising:
   a first voltage divider circuit capable of generating a first reference voltage signal;
   a second voltage divider circuit capable of generating a second reference voltage signal; and
   a differential amplifier receiving said first reference voltage signal and said second reference voltage signal as input signals, and for generating an output signal, said output signal representing a difference between said first reference voltage signal and said second reference voltage signal;
   wherein said second voltage divider circuit includes a first floating gate transistor comprising a floating gate terminal having a known DNA sample disposed thereon and capable of receiving said unknown DNA sample, said first floating gate transistor having a conductance value which varies if hybridization occurs between said known DNA sample and said unknown DNA sample when said unknown DNA sample is delivered to said floating gate terminal of said first floating gate transistor, and
   wherein in said known DNA sample has a highly negative charged molecule attached thereto.

8. The biosensor cell of claim 7, wherein a variation in said conductance value of said first floating gate transistor causes an increase in the amount of current flowing through said first floating gate transistor, which causes a corresponding variation in said second reference voltage signal.

9. The biosensor cell of claim 7, wherein said output signal has an amplitude which varies in accordance with variations of said conductance value of said first floating gate transistor.

10. The biosensor cell of claim 7, further comprising:
   a first pass transistor operative for coupling a voltage supply to said first voltage divider and said second voltage divider; and
   a second pass transistor operative for coupling an output of said differential amplifier to an output port of said biosensor cell;
   said first pass transistor and said second pass transistor being activated by external control signals.

11. The biosensor cell of claim 7, wherein hybridization of said known DNA sample and said unknown DNA sample causes an increase in a charge on said floating gate terminal of said first floating gate transistor, said increase in said charge on said floating gate terminal generating an increase in said conductance value of said first floating gate transistor.

12. The biosensor cell of claim 7, wherein said first voltage divider circuit includes a second floating gate transistor having said known DNA sample disposed on a floating gate terminal of said second floating gate transistor, said second floating gate transistor comprising the same amount of the known DNA sample as said first floating gate transistor such that said first reference voltage signal and said second reference voltage signal are equal if said known DNA sample and said unknown DNA sample do not hybridize in said first floating gate transistor.

13. A biosensor cell for identifying an unknown DNA sample, said cell comprising:
   means for generating a first reference voltage signal;
   means for generating a second reference voltage signal; and
   means for receiving said first reference voltage signal and said second reference voltage signal as input signals, and for generating an output signal, said output signal representing a difference between said first reference voltage signal and said second reference voltage signal;
   wherein said means for generating said first reference voltage includes a first floating gate transistor comprising a floating gate terminal having a known DNA sample disposed thereon and capable of receiving said unknown DNA sample, said first floating gate transistor having a conductance value which varies if hybridization occurs between said known DNA sample and said unknown DNA sample when said unknown DNA sample is delivered to said first floating gate terminal of said first floating gate transistor, and
   wherein in said known DNA sample has a highly negative charged molecule attached thereto.

14. The biosensor cell of claim 13, wherein a variation in said conductance value of said first floating gate transistor causes a corresponding variation in said second reference voltage signal.

15. The biosensor cell of claim 13, wherein hybridization of said known DNA sample and said unknown DNA sample causes an increase in a charge on said floating gate terminal of said first floating gate transistor, said increase in said charge on said floating gate terminal generating an increase in said conductance value of said first floating gate transistor.

16. The biosensor cell of claim 13, wherein said means for generating a first reference signal includes a second floating gate transistor having said known DNA sample disposed on a floating gate terminal of said second floating gate transistor, said second floating gate transistor comprising the same amount of the known DNA sample as said first floating gate transistor such that said first reference voltage signal and said second reference voltage signal are equal if said known DNA sample and said unknown DNA sample do not hybridize in said first floating gate transistor.

17. A method of identifying an unknown DNA sample, said method comprising the steps of:
   generating a first reference voltage signal;
   generating a second reference voltage signal utilizing a first floating gate transistor having a floating gate terminal, said floating gate terminal having a known DNA sample disposed thereon and capable of receiving said unknown DNA sample, said first floating gate transistor having a conductance value which varies if hybridization occurs between said known DNA sample and said unknown DNA sample when said unknown DNA sample is delivered to said floating gate terminal; and
   generating an output signal representing a difference between said first reference voltage signal and said second reference voltage signal,
   wherein in said known DNA sample has a highly negative charged molecule attached thereto.

18. The method of claim 17, wherein a variation in said conductance value of said first floating gate transistor causes a corresponding variation in said second reference voltage signal.

19. The method of claim 17, wherein hybridization of said known DNA sample and said unknown DNA sample causes an increase in a charge on said floating gate terminal of said first floating gate transistor, said increase in said charge on said floating gate terminal generating an increase in said conductance value of said first floating gate transistor.

20. The method of claim 17, wherein said method of generating a first reference signal includes a second floating gate transistor having said known DNA sample disposed on a floating gate terminal of said second floating gate transistor, said second floating gate transistor comprising the same amount of the known DNA sample as said first floating gate transistor such that said first reference voltage signal and said second reference voltage signal are equal if said known DNA sample and said unknown DNA sample do not hybridize in said first floating gate transistor.

* * * * *